US005643555A

United States Patent [19]
Collin et al.

[11] Patent Number: 5,643,555
[45] Date of Patent: Jul. 1, 1997

[54] SURFACTANT-FREE WATER-IN-OIL EMULSION

[75] Inventors: Nathalie Collin, Sceaux; Didier Candau, Bievres, both of France

[73] Assignee: L'Oreal, Paris, France

[21] Appl. No.: 467,400

[22] Filed: Jun. 6, 1995

[30] Foreign Application Priority Data

Jun. 6, 1994 [FR] France ................... 94 06899

[51] Int. Cl.$^6$ .................................. A61K 7/021
[52] U.S. Cl. ................. 424/59; 424/63; 424/70.121; 524/837
[58] Field of Search ............ 424/63, 59, 70.121; 524/837

[56] References Cited

U.S. PATENT DOCUMENTS 4,892,726  1/1990  Yonekura et al. ............... 424/63
5,036,108  7/1991  Asahi et al. ..................... 514/937

FOREIGN PATENT DOCUMENTS

A-2208642  6/1974  France .

OTHER PUBLICATIONS

S. Levine, "Stabilization of Emulsions by Fine Particles I. Partitioning of Particles Between Continuous Phase and Oil/Water Interface", *Colloids and Surfaces*, vol. 38, 1989, pp. 325–343.

Patent Abstracts of Japan, vol. 14, No. 30 (C–678) (3973), Jan. 19, 1990 & JP-A-01 268 615 (KAO Corporation) Oct. 26, 1989, (one page).

S. Magdassi, "Chitin Particles as O/W Emulsion Stabilizers", *J. Dispersion Science and Technology*, vol. 11, No. 1, 1990, pp. 69–74.

Hawley's Condensed Chemical Distionary, pp. 461, 566 and 567 1993.

*Primary Examiner*—Margaret W. Glass
*Attorney, Agent, or Firm*—Oblon, Spivak, McClelland, Maier & Neustadt, P.C.

[57] ABSTRACT

An emulsion of an aqueous phase in an oily phase free from surfactant, containing finely divided solid spherical particles of polyalkylsilsesquioxane which ensure the dispersion of the aqueous phase in the oily phase.

19 Claims, 1 Drawing Sheet

SURFACTANT-FREE WATER-IN-OIL EMULSION

FIELD OF THE INVENTION

The present invention relates to a new water-in-oil (W/O) emulsion comprising no surfactant. This emulsion is preferably in the form of a white or colored cream intended especially for the cosmetic treatment of the skin (body, face, etc). This cream may furthermore be used for the dermatological treatment of the skin.

BACKGROUND OF THE INVENTION

In the field of cosmetics it is commonplace to employ creams consisting of a water-in-oil emulsion because they make it possible to form a film at the surface of the skin which prevents the transepidermic loss of water and protects the skin against external attacks. These emulsions comprise an aqueous phase dispersed in an oily phase and a surfactant which stabilizes the dispersion. They have the disadvantage of containing surfactants; it is known that surfactants may irritate certain types of skin.

Furthermore, these emulsions conventionally contain from 25% to 30% by weight of oil relative to the total weight of the emulsion, and this percentage is often found to be insufficient when it is desired to incorporate a large quantity of lipophilic active substances. In addition, when an emulsion contains a fairly high proportion of oil, it appears very greasy to the user, all the more so since the outer phase of the emulsion is the fatty phase.

OBJECTS OF THE INVENTION

There is therefore a continuing need for a water-in-oil emulsion not exhibiting the disadvantages encountered with those known hitherto, especially not containing any surfactant and comprising a large quantity of oil without having the fatty feeling when applied.

The emulsion according to the invention enables precisely to overcome the disadvantages described above. In fact, it has unexpectedly been found that it is possible to obtain a water-in-oil emulsion without the use of a surfactant by employing spherical silicone-containing particles which stabilize the emulsion. The latter have a pleasant texture, a powdery and very soft feel and a cool effect despite a large quantity of oil.

DETAILED DESCRIPTION OF THE INVENTION

Figure 1:
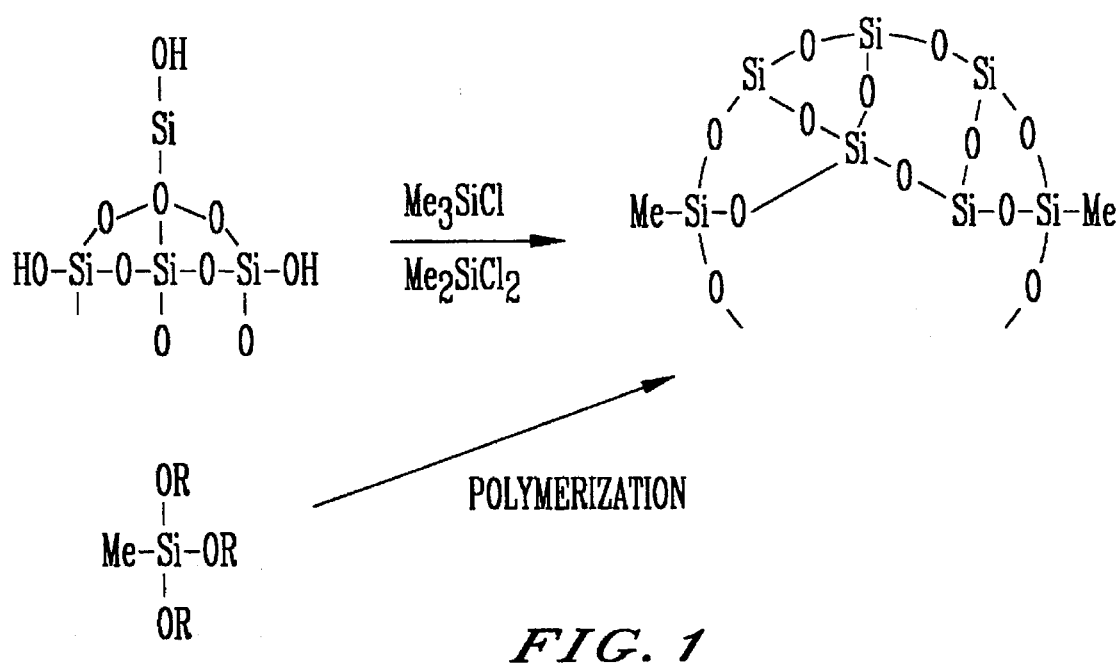
FIG. 1 depicts processes for preparing particles of formula (A).

The present invention is directed to an emulsion of an aqueous phase in an oily phase, containing finely divided solid spherical particles of polyalkylsilsesquioxane, characterized in that it is free from surfactant, the particles ensuring the dispersion of the aqueous phase in the oily phase, preferably containing water globules having a diameter of 100 nm to 20 µm. In addition, it advantageously contains a cosmetically and/or pharmaceutically acceptable medium.

Another embodiment of the present invention is the emulsion defined above for the cosmetic treatment of the skin (nutrition, hydration, protection, etc.) and for the preparation of a cream intended for the treatment of skin diseases (dry skin, etc.).

A further embodiment of the present invention is a process for the cosmetic treatment of the skin, comprising applying the emulsion defined above to the skin.

It is known from the paper by C. Levine (Colloids and Surfaces, 1989, Volume 38, pages 325 to 343, "Stabilization of emulsions by fine particles. I. Partitioning of particles between continuous phase and oil/water interface" incorporated herein by reference) to employ fine silica particles made hydrophobic by surface treatment in order to stabilize dispersions containing no surfactant. However, this document does not lead a person of ordinary skill in the cosmetic field to the present invention, because on the one hand it relates to a quite different technical field (heavy oils and bitumens) and, on the other hand, because the teaching which is given therein leads to a three-phase liquid system and not to a homogeneous system. In addition, the dispersions obtained by Levine are coarse dispersions in which the droplets are visible to the naked eye. A cosmetic emulsion, by definition, is a fine and homogeneous dispersion of two phases, one in the other, in which the globules in practice have a diameter of 100 nm to 20 µm. There was therefore no reason for a person skilled in the art to employ such particles for stabilizing a cosmetic emulsion, all the more so since it is well known that an emulsion breaks very easily as soon as the constituents thereof and/or their proportions are modified.

FR-A-2208642 discloses a liquid cosmetic composition with two different phases, one consisting of water and an organic solvent (ethanol or propanol) and the other consisting of oil, finely divided particles being situated at the interface of the two phases. The particles consist of inorganic substances or synthetic organic substances such as polyvinyl chloride. These particles are intended to facilitate the formation of the beads of oil in the hydroalcoholic medium.

Because of the type of product obtained, namely, a two-phase composition, and because of the presence of alcohol, this document does not lead a person of ordinary skill in the art to employ silicone-containing particles in order to stabilize a water-in-oil emulsion comprising no alcohol. In the present invention an attempt is made to obtain a homogeneous emulsion having the least amount of irritant possible, and therefore without alcohol, and not a two-phase composition containing alcohol or surfactants which can be irritating. Moreover, by their very nature and their size, the particles described in document FR-A-2208642 differ from those which make it possible to emulsify water in oil according to the present invention.

The present invention emulsion preferably comprises polyalkylsilsesquioxane particles for dispersing an aqueous phase in an oily phase and stabilizing the surfactant-free emulsion obtained, where globules preferably have a diameter of 100 nm to 20 µm. The particles according to the present invention are preferably spherical and preferably obtained either by surface treatment of pyrogenic silicas or by polymerization of an alkoxyalkylsilane. These processes produce particles corresponding to formula A, given in FIG. 1.

The surface treatment of pyrogenic silicas can be carried out with the aid of optionally alkylsilyl halide in which the alkyl radical contains from 1 to 4 carbon atoms. The alkyl radical is preferably a methyl group. The surface treatment is, for example, preferably carried out with a methylsilane or a methylsilyl halide, and in particular $Me_3SiCl$, $Me_2SiCl_2$ or $MeSiCl_3$. Particles of this type which can be employed in the present invention include those sold by Degussa under the names Aerosil R805, Aerosil R812 and Aerosil R974.

The polymerization of alkoxyalkylsilane may be carried out by starting from an alkoxyalkylsilane in which the alkoxy group contains from 1 to 5 carbon atoms and in which the alkyl group contains from 1 to 4 carbon atoms. It is preferably a trialkoxymethylsilane and, better still, trimethoxymethylsilane. Such a polymerization process is described in EP-293795. Particles of this type which can be employed in the invention include those sold by Toshiba under the names of Tospearl 103, Tospearl 105 and Tospearl 108.

These particles are known to impart good spreading and antiseptic properties to compositions which contain them, and reference may be made on this subject to JP-A-05148120, incorporated herein by reference. However, it is to be noted that the use of surfactants is indispensable in this document. In addition, not all the polyalkylsilsesquioxane particles mentioned in this document are suitable for stabilizing an emulsion, as shown by the comparative examples given below.

To enable an emulsion to be stabilized, the polyalkylsilsesquioxane particles useful in the present invention should have a diameter ranging from 7 to 800 nm, and preferably a diameter smaller than 14 nm and, for example, from 7 to 12 nm when obtained by surface treatment of pyrogenic silica, and a diameter of 100 to 800 nm when they are obtained by polymerization of an alkoxyalkylsilane. These diameter ranges include all values and all sub-ranges therebetween.

The emulsion according to the present invention preferably comprises, for example, from 1% to 20% by weight of particles in relation to the total weight of the emulsion, and preferably from 1% to 10%, and, better, from 2% to 5% by weight, including all values and all sub-ranges therebetween. The quantity of oil which may be introduced into the invention emulsion may represent from 40% to 80% by weight relative to the total weight of the emulsion. In practice it depends on the source of the particles.

When the particles are obtained by surface treatment of pyrogenic silica the oily phase of the present invention emulsion may range from 50% to 80% by weight relative to the total weight of the emulsion and, better, from 60% to 75% by weight. When the particles are obtained by alkoxyalkylsilane polymerization the oily phase of the present invention emulsion may range from 40% to 60% by weight relative to the total weight of the emulsion and, better, from 45% to 55% by weight.

In general, if it is intended to incorporate more oil than that amount described above, an lipophilic gelling agent may be added, which makes it possible to increase the quantity of oil while maintaining good emulsion stability and while avoiding a greasy appearance when this emulsion is applied to the skin. Lipophilic gelling agents which may be used include modified clays such as bentones, metal salts of fatty acids, such as aluminum stearate, and hydrophobic silica and glycol stearate esters such as the acetylated glycol stearate ester sold by Guardian under the name of Unitwix.

Oils useful in the present invention emulsion include vegetable oils, fruit oils (e.g., apricot oil), oils of animal origin, mineral oils (e.g., vaseline oil), synthetic oils (e.g., isopropyl myristate, octyl palmitate), silicone oils and/or fluorinated oils. Organic solvents such as $C_1$–$C_5$ alcohols, acetone, ether, hexane, etc. are excluded. Oils which are nonpolar and/or of low molecular weight are preferably employed, and especially light oils such as isohexadecane and volatile silicones, for example cyclomethicones. The light oils are those which have a viscosity lower than or equal to 0.015 Pa s. Oils which are nonpolar and/or exhibit a viscosity lower than or equal to 0.015 Pa s preferably represent at least 50% by weight of the oily phase. To improve the consistency of the invention emulsion, the oily phase of the emulsion may, in addition, contain other fatty substances such as fatty acids, fatty alcohols and waxes.

The emulsions forming the subject of the present invention find their application in a large number of cosmetic and/or dermatological treatments of the skin, including the scalp, especially for skin care and make-up. The invention emulsions may contain adjuvants which are typical in the field of cosmetics, such as hydrophilic or lipophilic active substances, stabilizers, antioxidants, perfumes, fillers, screening agents, colorant substances, lipid vesicles, etc. Depending on their nature, these adjuvants are employed in their usual proportions for emulsions and, for example, from 0.01% to 10% by weight relative to the total weight of the emulsion. Depending on their nature, they are introduced into the aqueous phase or into the oily phase of the emulsion.

As a result of the possible presence of a large quantity of oil in the invention emulsion, it is easier to incorporate lipophilic active substances therein. Lipophilic active substances useful in the invention include liposoluble vitamins such as tocopherol (vitamin E) and its esters, retinol (vitamin A) and its esters and vitamin F.

The following examples of compositions according to the invention are given by way of illustration and without any limitation being implied. The quantities are given therein in % by weight.

EXAMPLE 1

Cream

| Oily phase: | |
|---|---|
| Cyclomethicone | 38.4% |
| Apricot oil | 5.0% |
| Polymethylsilsesquioxane particles (Tospearl 103 sold by Toshiba - diameter: 300 nm) | 5.0% |
| Propylparaben (stabilizer) | 0.1% |
| Aqueous phase: | |
| Glycerin | 3.0% |
| Methylparaben (stabilizer) | 0.2% |
| Water | q.s. 100.0% |

The polymethylsilsesquioxane particles were dispersed in the oily phase, with magnetic stirring, at a temperature of 25° C. and then the aqueous phase was introduced into the oily phase thus obtained, with stirring at high speed with a Moritz (3000 revolutions/minute).

A fine fluid emulsion is obtained in which the water globules have a diameter of approximately 1 μm, usable especially as a day cream.

COMPARATIVE EXAMPLE 1

| Oily phase: | |
|---|---|
| Cyclomethicone | 38.4% |
| Apricot oil | 5.0% |
| Polymethylsilsesquioxane particles (Tospearl 240 sold by Toshiba - diameter: 4000 nm) | 5.0% |

| Propylparaben (stabilizer) | 0.1% |
| --- | --- |
| Aqueous phase: | |
| Glycerin | 3.0% |
| Methylparaben (stabilizer) | 0.2% |
| Water | q.s. 100.0% |

The preparation method was the same as in Example 1.

A very coarse emulsion was obtained in which the water globules have a diameter of 10 to 50 μm, in which salting-out of the oil takes place: the oil separates from the emulsion and rises to the surface.

EXAMPLE 2

Cream

| Oily phase: | |
| --- | --- |
| Cyclomethicone | 66.9% |
| Apricot oil | 5.0% |
| Polymethylsilsesquioxane particles (Aerosil R812, sold by Degussa - diameter: 7 nm) | 5.0% |
| Propylparaben (stabilizer) | 0.1% |
| Aqueous phase: | |
| Glycerin | 3.0% |
| Methylparaben (stabilizer) | 0.2% |
| Water | q.s. 100.0% |

The preparation method was the same as that in Example 1. A fine fluid emulsion is obtained in which the water globules have a diameter of approximately 800 nm, which was quite stable.

COMPARATIVE EXAMPLE 2

| Oily phase: | |
| --- | --- |
| Cyclomethicone | 66.9% |
| Apricot oil | 5.0% |
| Polymethylsilsesquioxane particles (Aerosil R972, sold by Degussa - diameter: 16 nm) | 5.0% |
| Propylparaben (stabilizer) | 0.1% |
| Aqueous phase: | |
| Glycerin | 3.0% |
| Methylparaben (stabilizer) | 0.2% |
| Water | q.s. 100.0% |

The preparation method was the same as that in Example 1. A coarse emulsion was obtained in which the water globules have a diameter of approximately 5 to 10 μm, in which salting-out of the oil takes place.

EXAMPLE 3

Cream

| Oily phase: | |
| --- | --- |
| Cyclomethicone | 28.4% |
| Apricot oil | 5.0% |
| Bentone | 10.0% |
| Polymethylsilsesquioxane particles (Tospearl 103, sold by Toshiba - diameter: 300 nm) | 3.5% |
| Propylparaben (stabilizer) | 0.1% |
| Aqueous phase: | |
| Glycerin | 3.0% |
| Methylparaben (stabilizer) | 0.2% |
| Water | q.s. 100.0% |

The process of preparation consisted of dispersing the polymethylsilsesquioxane particles in the oily phase not containing the bentone, with magnetic stirring at a temperature of 25° C., next pouring the aqueous phase into the oily phase thus obtained with stirring at high speed using the Moritz (3000 revolutions/minute), and then adding the bentone.

A fine emulsion was obtained in which the water globules have a diameter of 800 nm and which forms a fairly thick gelled white cream usable especially as a day cream. It is particularly suitable for normal and dry skin.

The cream obtained was tested by a panel of 31 persons specialized in the field of cosmetics who applied it to the face and kept it for the whole day. The cream was judged comfortable to apply, not sticky, not very greasy and soft.

This application is based on French Patent 2720644 incorporated herein by reference.

What is claimed as new and desired to be secured by Letters Patent of the United States is:

1. An emulsion comprising an aqueous phase, an oily phase, and particles of polyalkylsilsesquioxane, wherein said emulsion is free from surfactant and contains water globules having a diameter of 100 nm to 20 μm.

2. The emulsion according to claim 1, wherein it is free from organic solvent.

3. The emulsion according to claim 1, wherein the polyalkylsilsesquioxane particles are obtained by a surface treatment of pyrogenic silica with an alkylsilane in which the alkyl group contains from 1 to 4 carbon atoms or an alkylsilyl halide.

4. The emulsion according to claim 3, wherein the alkylsilyl halide is a methylsilyl halide.

5. The emulsion according to claim 1, wherein the particles have a diameter of less than 14 nm.

6. The emulsion according to claim 1, wherein the polyalkylsilsesquioxane particles are obtained by polymerization of an alkoxyalkylsilane.

7. The emulsion according to claim 6, wherein the alkoxyalkylsilane is a trialkoxymethylsilane in which the alkoxy group contains from 1 to 5 carbon atoms.

8. The emulsion according to claim 1, wherein the particles have a diameter of 100 nm to 800 nm.

9. The emulsion according to claim 6, wherein the particles have a diameter of 100 nm to 800 nm.

10. The emulsion according to claim 1, wherein the particles represent from 1% to 20% by weight relative to the total weight of the emulsion.

11. The emulsion according to claim 1, wherein the particles represent from 1% to 10% by weight relative to the total weight of the emulsion.

12. The emulsion according to claim 1, wherein the oily phase represents from 40% to 80% by weight relative to the total weight of the emulsion.

13. The emulsion according to claim 1, wherein the oily phase contains an oil which is nonpolar and/or has a viscosity lower than 0.015 Pa s.

14. The emulsion according to claim 13, wherein the oil which is nonpolar and/or has a viscosity lower than 0.015 Pa s is a volatile silicone.

15. The emulsion according to claim 13, wherein the oil which is nonpolar and/or has a viscosity lower than 0.015 Pa s represents at least 50% by weight of the oily phase.

16. The emulsion according to claim 1, further comprising at least one additive selected from the group consisting of lipophilic gelling agents, hydrophilic active substances, lipophilic active substances, stabilizers, antioxidants, perfumes, fillers, screening agents, colorant substances and lipid vesicles.

17. A cosmetic and/or dermatological composition comprising the emulsion of claim 1.

18. A cosmetic treatment process comprising applying to the skin the emulsion according to claim 1.

19. A method for dispersing an aqueous phase in an oily phase and stabilizing a surfactant-free emulsion having water globules with a diameter of 100 nm to 20 μm comprising mixing an aqueous phase, an oily phase and polyalkylsilsesquioxane particles together.

* * * * *